United States Patent
Araki et al.

(10) Patent No.: US 7,304,075 B2
(45) Date of Patent: Dec. 4, 2007

(54) STABILIZED LIQUID PREPARATION

(75) Inventors: Masanori Araki, Haibara-gun (JP);
Hiroaki Nakagami, Edogawa-ku (JP);
Azusa Matsukawa, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 131 days.

(21) Appl. No.: 10/258,447

(22) PCT Filed: Apr. 23, 2001

(86) PCT No.: PCT/JP01/03457

§ 371 (c)(1),
(2), (4) Date: Oct. 24, 2002

(87) PCT Pub. No.: WO01/80858

PCT Pub. Date: Nov. 1, 2001

(65) Prior Publication Data

US 2003/0139436 A1 Jul. 24, 2003

(51) Int. Cl.
*A01N 43/42* (2006.01)
(52) U.S. Cl. ...................... 514/312; 514/278
(58) Field of Classification Search ............... 514/312, 514/278, 212, 254
See application file for complete search history.

(56) References Cited

U.S. PATENT DOCUMENTS 4,957,922 A 9/1990 Lammens et al.
5,587,386 A * 12/1996 Hayakawa et al. ......... 514/312

FOREIGN PATENT DOCUMENTS

EP 0 341 493 A2 11/1989
EP 0470252 A1 2/1992
RU 2044544 4/2006

OTHER PUBLICATIONS

CAS STN Registry for Perfloxacin and ciprofloxacin, p. 1-2.*
CA on STN, AN 119:233801, Bails, M. et al., "Pefloxacin Stability in Perfusion Solutions. Effect of Solvent and Filtration", J. Pharm. Clin., (1991), vol. 10, No. 4, pp. 247-250.
CA on STN, AN 121:163853, Hu, Daode, et al., "Stability of Ofloxacin in Several Transfusion Solutions", Zhongguo Yiyuan Yaoxue Zazhi, (1994), vol. 14, No. 4, pp. 168-169.
Tetsu Morimura et al., Photoreaction and Active Oxygen Generation by Photosensitization of a New Antibacterial Fluoroquinolone Derivatives, Orbifloxacin, in the Presence of Chloride Ion, Chem. Pharm. Bull. 45(11), (1997), pp. 1828-1832.
M. Bails, et al., The Stability of Pefloxacin in Solution for IV Admixture: Effect of the Solvent and of Filtration, Journal of Pharm. Clin. 1991; 10: pp. 247-250, Paris, France.
D. Hu et al., The Observation on Stability of Ofloxacin Injection in Several Transfusion Fluids, Pharmaceutical Department, Hospital of Xuzhou Medical College, pp. 1-4, Jiangsu Province, Japan.
Mao, Youchang et al., "Stability of 1% ofloxacin injection in several transfusion solutions", Database CA 'Online! Chemical Abstracts Service, Columbus, Ohio, US, 1997, retrieved rom STN Dataabase accession No. 1997:532254; XP-002366393.
Miyazaki, Shuichi, et al, "In vitro and in vivo evaluation of DU6859a, a new flourouquinolone among injectable antibacterials tested against clinical isolates" Journal of Injection and Chemotherapy, 2(3), 148-155, 1996 XP00906974.
Tomioka, H. et al., "Comparative in Vitro Antimicrobial Activities of the Newly Synthesized Quinolone HSR-903, Sitaflaxocin (DU-6859A), Gatifloxacin (AM-1155), and Levofloxacin Against Mycobacterium Tuberculosis and Mucobacterium Avium Complex" Antimicrobial Agents and Chemotherapy, American Society for Microbiology, Washington, D.D., US, vol. 43, No. 12, Dec. 1999, pp. 3001-3004, XP002941445.

* cited by examiner

*Primary Examiner*—San-Ming Hui
(74) *Attorney, Agent, or Firm*—Sughrue Mion Pllc.

(57) ABSTRACT

A liquid preparation having improved light stability is provided, which comprises an aqueous solution containing sitafloxacin and sodium chloride.

43 Claims, No Drawings

STABILIZED LIQUID PREPARATION

TECHNICAL FIELD

This invention relates to a liquid preparation comprising an antimicrobial agent aqueous solution having improved light stability and a process for producing the same.

BACKGROUND ART

Sitafloxacin (name according to International Nonproprietary Names (INN)) is a compound having the chemical structure shown below that was granted a patent in Japan (Japanese Patent No. 2714597).

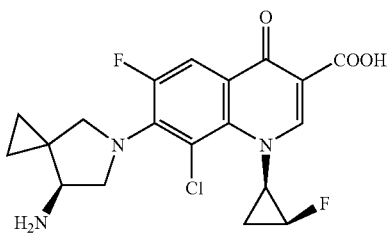

This compound exhibits very high antimicrobial activities and high safety and has been under study with expectation for application as an excellent quinolone synthetic antimicrobial agent.

Sitafloxacin is a promising antimicrobial agent having potent antimicrobial activities, especially in the treatment of serious infectious diseases. Therefore, it is desirable that sitafloxacin is available in a formulation suited to not only orally but also parenterally. The present inventors have researched into preparation of a liquid preparation comprising an aqueous sitafloxacin solution. It has turned out as a result that sitafloxacin in aqueous solution lacks stability to light. Specifically they have revealed that sitafloxacin in aqueous solution undergoes decomposition on being irradiated with light, resulting in reductions of sitafloxacin content, pH, and light transmission. Formation of sitafloxacin related substances was also determined. Namely, it has been revealed that the light stability of an aqueous sitafloxacin solution needs to be improved in order to supply a liquid preparation comprising an aqueous sitafloxacin solution.

DISCLOSURE OF INVENTION

As a result of extensive investigations, the present inventors have found that sitafloxacin in aqueous solution is prevented from decomposing on irradiation in the presence of sodium chloride. They have ascertained that reductions in sitafloxacin content, pH and light transmission of an aqueous sitafloxacin solution and formation of related substances are suppressed in the presence of sodium chloride. The present invention has been reached to completion based on these findings.

That is, the present invention relates to a (anitimicrobial) liquid preparation comprising an aqueous solution containing sitafloxacin and sodium chloride.

Also, the present invention relates to a liquid preparation comprising an aqueous solution containing a compound represented by formula:

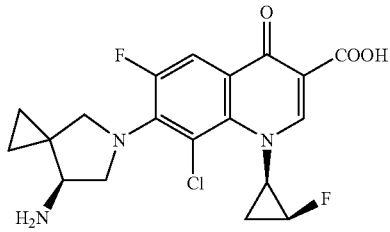

and sodium chloride.

Further, the present invention relates to a liquid preparation comprising an aqueous solution containing (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid and sodium chloride.

The present invention also relates to the following embodiments:

the above-mentioned liquid preparation, wherein sodium chloride content is 0.01 to 10% by weight;

the above-mentioned liquid preparation, wherein sodium chloride content is 0.01 to 5% by weight;

the above-mentioned liquid preparation, wherein sodium chloride content is 0.05 to 3% by weight;

the above-mentioned liquid preparation, wherein sodium chloride content is 0.50 to 1% by weight;

the above-mentioned liquid preparation, wherein the pH of the aqueous solution is 3.5 to 4.5, and the above-mentioned liquid preparation, wherein the pH of the aqueous solution is 3.8 to 4.2.

The present invention further relates to the following processes for preparing of the above-mentioned liquid preparations:

a process for preparing a liquid preparation comprising the steps of:

(1) preparing an acidic aqueous solution having dissolved therein sitafloxacin or a hydrate thereof and sodium chloride and (2) adjusting the pH of the acidic aqueous solution;

a process for preparing a liquid preparation comprising the steps of:

(1) preparing an acidic aqueous solution having dissolved therein a compound represented by formula:

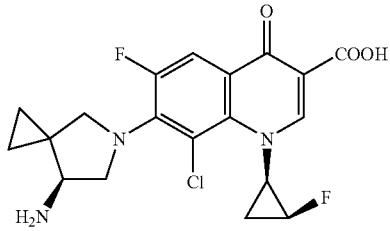

or a hydrate thereof and sodium chloride and (2) adjusting the pH of the acidic aqueous solution;

a process for preparing a liquid preparation comprising the steps of:

(1) preparing an acidic aqueous solution having dissolved therein (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid or a hydrate thereof and sodium chloride and (2) adjusting the pH of the acidic aqueous solution;

the above-mentioned process for preparing a liquid preparation, wherein the acidic aqueous solution is a hydrochloric acidic aqueous solution;

a process for preparing a liquid preparation comprising the steps of:

(1) preparing an aqueous solution having dissolved therein a sitafloxacin salt or a hydrate thereof and sodium chloride and (2) adjusting the pH of the aqueous solution;

the above-mentioned process for preparing a liquid preparation, wherein the sitafloxacin salt is a hydrochloride, a nitrate, a benzenesulfonate, a methanesulfonate or a toluenesulfonate;

a process for preparing a liquid preparation comprising the steps of:

(1) preparing an aqueous solution having dissolved therein a salt of a compound represented by formula:

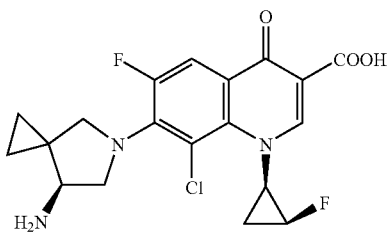

or a hydrate thereof and sodium chloride and (2) adjusting the pH of the aqueous solution;

the above-mentioned process for preparing a liquid preparation, wherein the salt of a compound represented by formula:

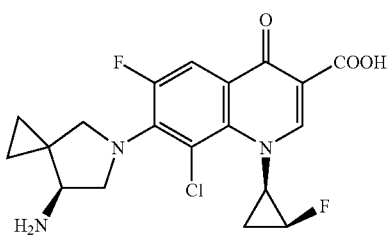

is a hydrochloride, a nitrate, a benzenesulfonate, a methanesulfonate or a toluenesulfonate;

a process for preparing a liquid preparation comprising the steps of:

(1) preparing an aqueous solution having dissolved therein a (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid salt or a hydrate thereof and sodium chloride and (2) adjusting the pH of the aqueous solution;

the above-mentioned process for preparing a liquid preparation, wherein the (−)-7-[(7S)-7-amino-5-azaspiro[2.4]hep-tan-5-yl]-8-chloro-6-fluoro-1-[(1R,2S)-2-fluoro-1-cyclopropyl]-1,4-dihydro-4-oxo-3-quinolinecarboxylic acid salt is a hydrochloride, a nitrate, a benzenesulfonate, a methanesulfonate or a toluenesulfonate;

the above-mentioned process for preparing a liquid preparation, wherein the step of adjusting the pH is carried out by addition of sodium hydroxide or an aqueous solution thereof;

the above-mentioned process for preparing a liquid preparation, wherein sodium chloride is present in an amount of 0.01 to 5% by weight;

the above-mentioned process for preparing a liquid preparation, wherein sodium chloride is present in an amount of 0.05 to 3% by weight;

the above-mentioned process for preparing a liquid preparation, wherein sodium chloride is present in an amount of 0.50 to 1% by weight;

the above-mentioned process for preparing a liquid preparation, wherein the step of adjusting the pH is a step of adjusting to a pH of 3.5 to 4.5; and the above-mentioned process for preparing a liquid preparation, wherein the step of adjusting the pH is a step of adjusting to a pH of 3.8 to 4.2.

Hereinafter, the present invention will be described in detail.

A stable liquid sitafloxacin preparation according to the present invention is prepared according to, for example, the following procedure.

Sitafloxacin (or its hydrate) is added to water for injection (hereinafter abbreviated as WFI), and sodium chloride is added thereto. Hydrochloric acid is added to the solution, followed by stirring or a like operation to dissolve sitafloxacin (or its hydrate) and sodium chloride. The pH of the resulting acidic aqueous solution is adjusted by addition of sodium hydroxide or an aqueous solution thereof, and WHI is added to make a predetermined amount of a liquid preparation.

Sitafloxacin is registered as "sitafloxacin hydrate" according to JAN (Japanese Accepted Names), which is a 3/2 hydrate free of addition of acid or base. The sitafloxacin as a raw material for preparing the liquid preparation of the invention includes not only the free hydrated compound but pharmaceutically acceptable acid addition salts and hydrates thereof. The pharmaceutically acceptable acid addition salts include inorganic acid salts, such as a hydrochloride and a nitrate, and organic acid salts, such as a methanesulfonate, a benzenesulfonate and a toluenesulfonate. In using the salt, the liquid preparation of the invention can be prepared by dissolving the salt in water and adding sodium chloride thereto. The pH of the aqueous solution can be adjusted according to necessary.

The aqueous solution thus prepared is sterilized and dispensed into containers. (Sterilization may follow dispensing.)

The sitafloxacin concentration of the aqueous solution is not particularly limited and can be selected according to the purpose of use and the method of use within a range of solubility of sitafloxacin in water (or water at a particular pH). A suitable concentration ranges from 0.1 to 20 mg/ml.

The sodium chloride content is usually selected from a range of 0.01 to 10% by weight. The liquid preparation comprising the aqueous sitafloxacin solution is characterized by containing sodium chloride by which the active ingredient, sitafloxacin, is stabilized against light. This light stabilizing effect of sodium chloride is observed even in a concentration as low as 0.01% by weight. It has been confirmed that the light stabilizing effect is enhanced with an increase of the sodium chloride concentration. An enhanced effect is obtained at a sodium chloride concentration of 0.05% or higher, and the effect is sustained at a further increased concentration. A particularly high stabilizing effect is obtained at a sodium chloride concentration of 0.1% or higher.

Addition of hydrochloric acid is for facilitating dissolution of free sitafloxacin because free sitafloxacin has poor water solubility around a neutral pH. Hydrochloric acid is usually added in excess within a range that is pharmaceutically acceptable and does not cause the active ingredient to decompose. Diluted hydrochloric acid, e.g., about 0.1 mol/l hydrochloric acid aqueous solution is used. The acid to be added is not limited to hydrochloric acid, and any other pharmaceutically acceptable acid that facilitates dissolution of sitafloxacin could be used.

Sodium hydroxide or an aqueous solution thereof is added to adjust the pH of the acidic solution. It is convenient for operation to use a diluted aqueous solution of sodium hydroxide, e.g., 0.1 mol/l aqueous sodium hydroxide, rather than to use sodium hydroxide in the form of solid or powder. Any base other than sodium hydroxide can be used as well for pH adjustment.

It is the most convenient to use hydrochloric acid as an acid and sodium hydroxide as a base in combination. The solution is adjusted to a pH of 3.5 to 4.5, preferably 3.7 to 4.2, still preferably about 4.

Further, the effect of the light stabilized preparation containing sodium chloride of the present invention is observed even at a higher pH. That is, it has been confirmed that the formation of related substances due to irradiation or the reduction in pH are more suppressed even in a sodium chloride-containing aqueous solution adjusted to about pH 8 than the aqueous solutions without sodium chloride. Therefore, the pH of the liquid preparation containing sodium chloride in the present invention is not particularly limited to the above-mentioned ranges and the upper limit thereof may be approximately 8.

In the final stage of the preparation of a liquid preparation, water is added to adjust to prescribed concentrations of the active ingredient and sodium chloride, which is a method commonly used in the art. Water as a solvent to be used for the preparation of a liquid preparation is not particularly limited as far as it is pharmaceutically acceptable, and WFI or its equivalence is used.

The sodium chloride-containing sitafloxacin aqueous solution thus prepared can be packed in a container for a single dose or for multiple doses. The container includes ampules, vials, plastic bags, syringes, etc.

Sterilization of the sitafloxacin preparations can be effected in a usual manner, for example, filtration or heating. Sterilization may be preceded or followed by packing into containers. If desired, the liquid preparation of the present invention can contain pharmaceutically acceptable additives, such as dissolving aids, buffering components, stabilizers, and the like.

The liquid preparation of the present invention can be used as not only systemic administration such as injections and drops but also topical administration such as liquids for external use and sprays.

BEST MODE FOR CARRYING OUT INVENTION

The present invention will be illustrated in greater detail with reference to the following Examples, but it is not intended that the present invention be limited thereto.

The sitafloxacin used was prepared by the applicant. The hydrochloric acid, sodium hydroxide, sodium chloride, and D-sorbitol were of JIS's guaranteed reagent grade. Water used was water for injection (WFI).

1) Samples Tested for Light Stability:

To 160 ml of WFI were added 213.2 mg of sitafloxacin (active ingredient: 200 mg) and a varied amount of sodium chloride (0 mg for control, 20 mg, 100 mg, 200 mg, 1 g, 2 g, 4 g, 6 g or 10 g) or, for comparison, 10 g of D-sorbitol. Further, 5 ml of 0.1 mol/l aqueous hydrochloric acid was slowly added, followed by stirring for 30 mintues to dissolve sitafloxacin and sodium chloride. The nine kinds of solution each was adjusted to pH 4.0 by addition of 0.1 mol/l aqueous sodium hydroxide, and WFI was added to make 200 ml. Ten milliliter portions of the resulting aqueous solution were put into colorless ampules.

2) Test Method:

a) Items and Method for the Evaluation of Light Stability
① pH: Measured with a pH meter (F-16, supplied by Horiba, Ltd.).
② Osmotic pressure: Measured with an osmometer (3C2, supplied by Advanced Instrument, Inc.).
③ (Light) Transmission: A transmission at 430 nm was measured with a Beckman DU-640 spectrophotometer.
④ Retention: The content of sitafloxacin of the irradiated samples was determined as follows to calculate retention (%).

A test solution was prepared by accurately measuring 2 ml of a sample, adding an accurately measured equal amount of an internal standard solution, adding a mobile phase to make 20 ml, and mixing a 5 ml aliquot of the resulting solution with the mobile phase to make 20 ml.

A standard sitafloxacin solution was prepared by dissolving sitafloxacin for quantitative analysis (whose water content had been measured previously) precisely weighing about 0.1 g in the mobile phase to make a solution accurately measuring 100 ml, adding to an accurate 5 ml aliquot of the solution an accurately measured equal amount of the internal standard solution, adding the mobile phase to make 100 ml, and after thoroughly stirring, filtering the solution through a membrane filter. The test solution and the standard solution each measuring 10 µl were subjected to liquid chromatography under the following conditions. Ratios of the peak areas of sitafloxacin of the test solution or the standard solution to the peak area of the internal standard, $Q_T$ and $Q_S$, were obtained, and the sitafloxacin content was determined according to the following equation.

Sitafloxacin ($C_{19}H_{18}ClF_2N_3O_3$) content (% to nominal amount)=amount ($mg$) of sitafloxacin for quantitative analysis (on dry basis)×($Q_T/Q_S$)× (¼)×(½s)×100 wherein;
4: amount (mg) of sitafloxacin in 2 ml preparation
½s: dilution coefficient Internal standard solution: methanol solution of ethyl p-hydroxybenzoate (1→4000)

Conditions of Chromatography:
Detector: UV absorption spectrophotometer (measuring wavelength: 254 nm)
Column: STR ODS-II (4.6 mmø×150 mm), available from Shimadzu Corp.
Column temperature: constant at around 40° C.

Mobile phase: phosphate buffer (pH 2.4)/acetonitrile mixture (4:1)

Flow rate: controlled so that the retention time of sitafloxacin may be about 13 minutes.

⑤ Related substances:

A standard solution was prepared by weighing 0.100 g of sitafloxacin for quantitative analysis (whose water content had been measured previously), adding a mobile phase to accurately make 100 ml, and adding the mobile phase to an accurately measured aliquot (1 ml) of the solution to make 100 ml.

A 10 μl aliquot of a sample and the standard solution was subjected to liquid chromatography under the following conditions, and the peak areas of the respective solutions were calculated by automatic integration to obtain the total content of sitafloxacin related substances.

Conditions of Chromatography:

Detector: UV spectrophotometer (measuring wavelength: 295 nm)

Column: STR ODS-II (4.6 mmø×250 mm), available from Shimadzu Corp.

Column temperature: constant at around 40° C.

Mobile phase: phosphate buffer (pH 2.4)/acetonitrile mixture (4:1)

Flow rate: controlled so that the retention time of sitafloxacin may be about 20 minutes.

3) Method for the Evaluation of Light Stability of Aqueous Sitafloxacin Solution:

Each of the 1 mg/ml aqueous solutions of sitafloxacin was irradiated with light of a white fluorescent tube (2500 lux×5 days: 300,000 lux·hr), and the same measurements as described above were repeated.

4) Results and Observations:

a) Light Stability of Sitafloxacin in Aqueous Solution

The effects of varied sodium chloride concentrations on light stabilization of aqueous sitafloxacin solution (1 mg/ml) are shown in Table 1 below. For comparison, the results of aqueous sitafloxacin solution containing 5% D-sorbitol in place of sodium chloride are also shown.

However, it is apparent that addition of sodium chloride suppresses these unfavorable changes due to irradiation, showing improvement on sitafloxacin stability against light.

Also, sodium chloride proved effective even in as low a concentration as 0.01%, and its stabilizing effect increases with concentration. An increase of the stabilizing effect with concentration is noticeable up to a 0.5% concentration. The stabilizing effect was similarly observed at sodium chloride concentrations higher than 0.5%.

In addition, a liquid preparation containing sodium chloride was prepared using levofloxacin, and the sodium chloride-containing liquid preparation was compared with the preparation without sodium chloride with respect to influences due to irradiation on levofloxacin. The levofloxacin used was prepared by the applicant.

5) Preparation of Levofloxacin Samples Tested for Light Stability:

Levofloxacin and hydrochloric acid were added to about 800 ml of WFI and then dissolved completely. The sodium chloride-containing preparation was prepared in the same manner by mixing levofloxacin, sodium chloride and hydrochloric acid, followed by dissolving it. To each hydrochloric acid aqueous solution was added sodium hydroxide to adjust to pH 4.0. Thereafter, WFI was added thereto so as to adjust each concentration of levofloxacin (prescribed value: 2 mg/ml) and sodium chloride (prescribed value: 0.9%) to the prescribed values, thereby to make 1 liter. The resulting aqueous solutions were put into ampules and sealed, followed by steam-sterilizing.

6) Method for the Evaluation of Light Stability of Aqueous Levofloxacin Solution:

Each of the 2 mg/ml aqueous solutions of levofloxacin was irradiated with light of a white fluorescent tube (2500 lux×10 days: 600, 000 lux·hr), and the same measurements as described above were repeated.

7) Results and Observations:

As is understood from Table 2, it can be seen that the extents of reductions in pH and formation of related sub-

TABLE 1

| NaCl Concentration (%) | Initial | | | Irradiated (300,000 lux · hr) | | | Retention (per Initial %) |
|---|---|---|---|---|---|---|---|
| | pH | Transmission (%) | Total Related substances (%) | pH | Transmission (%) | Total Related Substances (%) | |
| 0 | 4.2 | 77.6 | 0.31 | 3.4 | 47.1 | 5.90 | 84.2 |
| 0.01 | 4.4 | 77.1 | 0.30 | 3.7 | 52.8 | 5.21 | 87.9 |
| 0.05 | 4.3 | 76.8 | 0.29 | 3.8 | 61.0 | 3.84 | 91.7 |
| 0.10 | 4.3 | 76.7 | 0.26 | 3.8 | 64.4 | 3.02 | 93.5 |
| 0.50 | 4.2 | 75.6 | 0.28 | 3.9 | 63.6 | 2.48 | 94.2 |
| 1.0 | 4.3 | 74.7 | 0.30 | 3.9 | 62.6 | 2.02 | 94.7 |
| 2.0 | 4.3 | 73.1 | 0.31 | 3.8 | 60.7 | 2.30 | 94.0 |
| 3.0 | 4.3 | 72.8 | 0.30 | 3.9 | 61.0 | 2.01 | 95.5 |
| 5.0 | 4.3 | 70.7 | 0.30 | 3.9 | 57.6 | 2.28 | 94.8 |
| D-sorb | 4.3 | 77.2 | 0.30 | 3.5 | 56.8 | 5.90 | 86.6 |

D-sorb: D-sorbitol
Transmission: T %, 430 nm

As is understood from Table 1, the aqueous sitafloxacin solutions without sodium chloride or containing D-sorbitol in place of sodium chloride undergo reductions in pH, transmission and sitafloxacin content and an increase of related substances when irradiated.

stances when irradiated are lower in the case of the sodium chloride-containing preparation. The results are shown in Table 2 below. That is, it is apparent that the effects of sodium chloride on light stabilization of an active ingredient in the liquid preparation containing sodium chloride is provided even if the active ingredient is levofloxacin and the stability of the active ingredient against irradiation can be maintained.

TABLE 2

| NaCl | Changes in pH | | Related Substances (total %) | |
| --- | --- | --- | --- | --- |
| | Initial | Irradiation | Initial | Irradiation |
| present | 4.27 | 3.94 | 0.15 | 2.45 |
| absent | 4.39 | 3.81 | 0.16 | 3.94 |

INDUSTRIAL APPLICABILITY

It was confirmed that light stability of a liquid preparation comprising an aqueous sitafloxacin solution is improved in the presence of sodium chloride. The light stability increases with an increase of sodium chloride concentration up to about 0.1% by weight. With the sodium chloride content on or above this level, the liquid preparation sustains light stability. Therefore, the preparation of the present invention is useful as a liquid preparation.

The invention claimed is:

1. A liquid preparation consisting of an aqueous solution of sitafloxacin, sodium chloride, and a pH adjusting agent selected from the group consisting of one or both of hydrochloric acid and sodium hydroxide.

2. A liquid preparation consisting of an aqueous solution of a compound represented by the following formula:

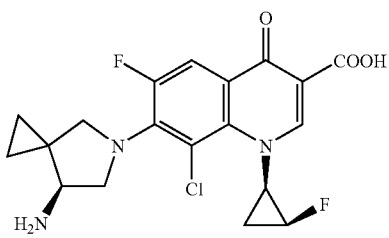

and sodium chloride.

3. A liquid preparation consisting of an aqueous solution of (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid and sodium chloride.

4. The liquid preparation according to any one of claims 1 to 3, wherein the sodium chloride is present in an amount of 0.01 to 10% by weight.

5. The liquid preparation according to any one of claims 1 to 3, wherein the sodium chloride is present in an amount of 0.01 to 5% by weight.

6. The liquid preparation according to any one of claims 1 to 3, wherein the sodium chloride is present in an amount of 0.05 to 3% by weight.

7. The liquid preparation according to any one of claims 1 to 3, wherein the sodium chloride is present in an amount of 0.50 to 1% by weight.

8. The liquid preparation according to any one of claims 1 to 3, wherein said aqueous solution has a pH of 3.5 to 4.5.

9. The liquid preparation according to any one of claims 1 to 3, wherein said aqueous solution has a pH of 3.8 to 4.2.

10. A process for preparing a liquid preparation consisting of the steps of:

(1) preparing an acidic aqueous solution of sitafloxacin or a hydrate thereof and sodium chloride and (2) adjusting the pH of said acidic aqueous solution.

11. A process for preparing a liquid preparation consisting of the steps of:

(1) preparing an acidic aqueous solution of a compound represented by the following formula:

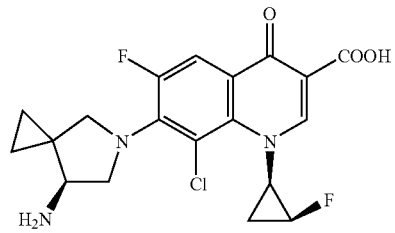

or a hydrate thereof and sodium chloride and (2) adjusting the pH of said acidic aqueous solution.

12. A process for preparing a liquid preparation consisting of the steps of:

(1) preparing an acidic aqueous solution of (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid or a hydrate thereof and sodium chloride and (2) adjusting the pH of said acidic aqueous solution.

13. The process for preparing a liquid preparation according to any one of claims 10 to 12, wherein said acidic aqueous solution is a hydrochloric acidic aqueous solution.

14. A process for preparing a liquid preparation consisting of the steps of:

(1) preparing an aqueous solution of a sitafloxacin salt or a hydrate thereof and sodium chloride and (2) adjusting the pH of said aqueous solution.

15. The process for preparing a liquid preparation according to claim 14, wherein said sitafloxacin salt is a hydrochloride, a nitrate, a benzenesulfonate, a methanesulfonate or a toluenesulfonate.

16. A process for preparing a liquid preparation consisting of the steps of:

(1) preparing an aqueous solution of a salt of a compound represented by the following formula:

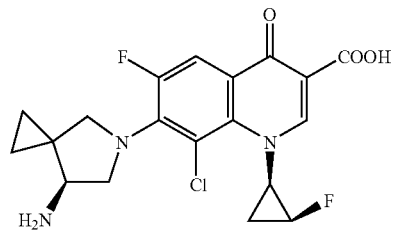

or a hydrate thereof and sodium chloride and (2) adjusting the pH of said aqueous solution.

17. The process for preparing a liquid preparation according to claim 16, wherein said salt of the compound represented by the following formula:

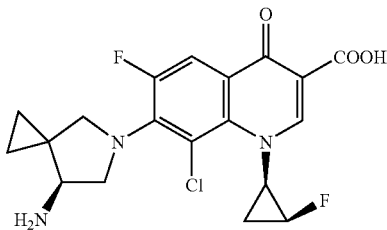

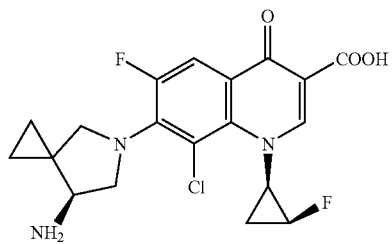

is a hydrochloride, a nitrate, a benzenesulfonate, a methanesulfonate or a toluenesulfonate.

18. A process for preparing a liquid preparation consisting of the steps of:
(1) preparing an aqueous solution of (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid salt or a hydrate thereof and sodium chloride and
(2) adjusting the pH of said aqueous solution.

19. The process for preparing a liquid preparation according to claim 18, wherein said (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid salt is a hydrochloride, a nitrate, a benzenesulfonate, a methanesulfonate or a toluenesulfonate.

20. The process for preparing a liquid preparation according to claim 10, 11, 12, 14 or 19, wherein said step of adjusting the pH is carried out by addition of sodium hydroxide or an aqueous solution thereof.

21. The process for preparing a liquid preparation according to claim 10, 11, 12, 14 or 19, wherein sodium chloride is present in an amount of 0.01 to 10% by weight.

22. The process for preparing a liquid preparation according to claim 10, 11, 12, 14 or 19, wherein sodium chloride is present in an amount of 0.01 to 5% by weight.

23. The process for preparing a liquid preparation according to claim 10, 11, 12, 14 or 19, wherein sodium chloride is present in an amount of 0.05 to 3% by weight.

24. The process for preparing a liquid preparation according to claim 10, 11, 12, 14 or 19, wherein sodium chloride is present in an amount of 0.50 to 1% by weight.

25. The process for preparing a liquid preparation according to claim 10, 11, 12, 14 or 19, wherein said step of adjusting the pH is a step of adjusting to a pH of 3.5 to 4.5.

26. The process for preparing a liquid preparation according to claim 10, 11, 12, 14 or 19, wherein said step of adjusting the pH is a step of adjusting to a pH of 3.8 to 4.2.

27. A process for stabilizing sitafloxacin against photo radiation, consisting of the steps of:
(1) preparing an acidic aqueous solution of sitafloxacin or a hydrate thereof and sodium chloride and
(2) adjusting the pH of said acidic aqueous solution.

28. A process for stabilizing sitafloxacin against photo radiation, consisting of the steps of:
(1) preparing an acidic aqueous solution of a compound represented by the following formula:

or a hydrate thereof and sodium chloride and
(2) adjusting the pH of said acidic aqueous solution.

29. A process for stabilizing sitafloxacin against photo radiation, consisting of the steps of:
(1) preparing an acidic aqueous solution of(−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid or a hydrate thereof and sodium chloride and
(2) adjusting the pH of said acidic aqueous solution.

30. The process according to any one of claims 27 to 29, wherein said acidic aqueous solution is a hydrochloric acidic aqueous solution.

31. A process for stabilizing sitafloxacin against photo radiation, consisting of the steps of:
(1) preparing an aqueous solution of a sitafloxacin salt or a hydrate thereof and sodium chloride and
(2) adjusting the pH of said aqueous solution.

32. The process according to claim 31, wherein said sitafloxacin salt is a hydrochloride, a nitrate, a benzenesulfonate, a methanesulfonate or a toluenesulfonate.

33. A process for stabilizing sitafloxacin against photo radiation, consisting of the steps of:
(1) preparing an aqueous solution of a salt of a compound represented by the following formula:

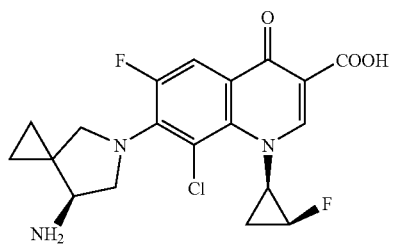

or a hydrate thereof and sodium chloride and
(2) adjusting the pH of said aqueous solution.

34. The process according to claim 33, wherein said salt of the compound represented by the following formula:

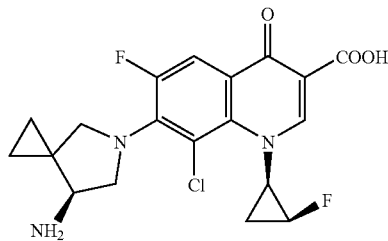

is a hydrochloride, a nitrate, a benzenesulfonate, a methanesulfonate or a toluenesulfonate.

35. A process for stabilizing sitafloxacin against photo radiation, consisting of the steps of:
(1) preparing an aqueous solution of (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid salt or a hydrate thereof and sodium chloride and
(2) adjusting the pH of said aqueous solution.

36. The process according to claim 35, wherein said (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid salt is a hydrochloride, a nitrate, a benzenesulfonate, a methanesulfonate or a toluenesulfonate.

37. The process according to claim 27, 28, 29, 31 or 36, wherein said step of adjusting the pH is carried out by addition of sodium hydroxide or an aqueous solution thereof.

38. The process according to claim 27, 28, 29, 31 or 36, wherein sodium chloride is present in an amount of 0.01 to 10% by weight.

39. The process according to claim 27, 28, 29, 31 or 36, wherein sodium chloride is present in an amount of 0.01 to 5% by weight.

40. The process according to claim 27, 28, 29, 31 or 36, wherein sodium chloride is present in an amount of 0.05 to 3% by weight.

41. The process according to claim 27, 28, 29, 31 or 36, wherein sodium chloride is present in an amount of 0.50 to 1% by weight.

42. The process according to claim 27, 28, 29, 31 or 36, wherein said step of adjusting the pH is a step of adjusting to a pH of 3.5 to 4.5.

43. The process according to claim 27, 28, 29, 31 or 36, wherein said step of adjusting the pH is a step of adjusting to a pH of 3.8 to 4.2.

* * * * *